US012616496B2

(12) United States Patent
Massimini et al.

(10) Patent No.: US 12,616,496 B2
(45) Date of Patent: May 5, 2026

(54) ATHERECTOMY SYSTEM WITH ANTEROGRADE AND RETROGRADE ABLATION

(71) Applicant: Boston Scientific Scimed, Inc., Maple Grove, MN (US)

(72) Inventors: Daniel Frank Massimini, Brooklyn Park, MN (US); Michael Kaland, Minneapolis, MN (US); Corydon Carlson, Stillwater, MN (US); Jarrod Kenneth Neuharth, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 726 days.

(21) Appl. No.: 17/894,033

(22) Filed: Aug. 23, 2022

(65) Prior Publication Data

US 2023/0069219 A1 Mar. 2, 2023

Related U.S. Application Data

(60) Provisional application No. 63/237,679, filed on Aug. 27, 2021.

(51) Int. Cl.
*A61B 17/3207* (2006.01)
*A61B 17/00* (2006.01)

(52) U.S. Cl.
CPC ................. *A61B 17/320758* (2013.01); *A61B 2017/00389* (2013.01); *A61B 2017/00477* (2013.01)

(58) Field of Classification Search
CPC ........ A61B 17/3207; A61B 17/320708; A61B 2017/320716; A61B 17/320725;
(Continued)

(56) References Cited

U.S. PATENT DOCUMENTS 2,088,654 A 8/1937 Hull
3,913,196 A 10/1975 Maday
(Continued)

FOREIGN PATENT DOCUMENTS

CA 2682488 A1 10/2008
DE 202005022017 U1 5/2012
(Continued)

OTHER PUBLICATIONS

International Search Report and Written Opinion dated Aug. 20, 2019 for International Application No. PCT/US2019/033748.
(Continued)

*Primary Examiner* — Thomas McEvoy
(74) *Attorney, Agent, or Firm* — Seager, Tufte & Wickhem, LLP

(57) ABSTRACT

An atherectomy system includes an advancer assembly and a drive assembly that is adapted to translate relative to the advancer assembly. A control knob extends from the drive assembly such that translating the control knob results in the drive assembly translating relative to the advancer assembly. A drive shaft is operably coupled with the drive assembly, the drive shaft translating relative to the advancer assembly as the drive assembly translates relative to the advancer assembly. A feedback modifier is operably coupled between the drive assembly and the advancer assembly and is adapted to provide a user of the atherectomy system with similar feedback via the control knob regardless of whether the user is moving the drive assembly in an anterograde ablation direction or a retrograde ablation direction.

17 Claims, 9 Drawing Sheets

(58) Field of Classification Search
CPC ....... A61B 2017/320733; A61B 2017/320741;
A61B 17/32075; A61B 17/320758; A61B
2017/320766; A61B 2017/320775; A61B
17/320783; A61B 2017/320791
See application file for complete search history.

(56) References Cited

U.S. PATENT DOCUMENTS

| | | | |
|---|---|---|---|
| 4,395,167 A | 7/1983 | Maternus | |
| 4,507,028 A | 3/1985 | Matsushita | |
| 4,679,557 A | 7/1987 | Opie et al. | |
| 5,116,350 A | 5/1992 | Stevens | |
| 5,287,858 A | 2/1994 | Hammerslag et al. | |
| 5,308,354 A | 5/1994 | Zacca et al. | |
| 5,314,407 A | 5/1994 | Auth et al. | |
| 5,417,703 A | 5/1995 | Brown et al. | |
| 5,478,344 A | 12/1995 | Stone et al. | |
| 5,501,694 A | 3/1996 | Ressemann et al. | |
| 5,540,707 A | 7/1996 | Ressemann et al. | |
| 5,563,481 A | 10/1996 | Krause | |
| 5,572,609 A | 11/1996 | Li | |
| 5,626,444 A | 5/1997 | Campian | |
| 5,632,755 A | 5/1997 | Nordgren et al. | |
| 5,674,235 A | 10/1997 | Parisi | |
| 5,681,336 A | 10/1997 | Clement et al. | |
| 5,709,661 A | 1/1998 | Van Egmond et al. | |
| 5,766,192 A | 6/1998 | Zacca | |
| 5,779,722 A | 7/1998 | Shturman et al. | |
| 5,823,990 A | 10/1998 | Henley | |
| 5,827,323 A | 10/1998 | Klieman et al. | |
| 5,836,868 A | 11/1998 | Ressemann et al. | |
| 5,899,915 A | 5/1999 | Saadat | |
| 5,913,867 A | 6/1999 | Dion | |
| 6,015,420 A | 1/2000 | Wulfman et al. | |
| 6,017,354 A | 1/2000 | Culp et al. | |
| 6,086,608 A | 7/2000 | Ek et al. | |
| 6,102,926 A | 8/2000 | Tartaglia et al. | |
| 6,106,301 A | 8/2000 | Merril | |
| 6,113,615 A | 9/2000 | Wulfman | |
| 6,120,515 A | 9/2000 | Rogers et al. | |
| 6,126,667 A | 10/2000 | Barry et al. | |
| 6,139,510 A | 10/2000 | Palermo | |
| 6,149,663 A | 11/2000 | Strandberg et al. | |
| 6,171,312 B1 | 1/2001 | Beaty | |
| 6,200,329 B1 | 3/2001 | Fung et al. | |
| 6,212,300 B1 | 4/2001 | Rengakuji | |
| 6,234,725 B1 | 5/2001 | Campian | |
| 6,270,509 B1 | 8/2001 | Barry et al. | |
| 6,312,438 B1 | 11/2001 | Adams | |
| 6,494,888 B1 | 12/2002 | Laufer et al. | |
| 6,500,186 B2 | 12/2002 | Lafontaine et al. | |
| 6,503,227 B1 | 1/2003 | Guo et al. | |
| 6,503,261 B1 | 1/2003 | Bruneau et al. | |
| 6,506,196 B1 | 1/2003 | Laufer | |
| 6,554,845 B1 | 4/2003 | Fleenor et al. | |
| 6,569,085 B2 | 5/2003 | Kortenbach et al. | |
| 6,579,298 B1 | 6/2003 | Peskin et al. | |
| 6,626,917 B1 | 9/2003 | Craig | |
| 6,632,230 B2 | 10/2003 | Barry | |
| 6,663,639 B1 | 12/2003 | Laufer et al. | |
| 6,719,763 B2 | 4/2004 | Chung et al. | |
| 6,740,030 B2 | 5/2004 | Martone et al. | |
| 6,746,457 B2 | 6/2004 | Dana et al. | |
| 6,755,843 B2 | 6/2004 | Chung et al. | |
| 6,773,441 B1 | 8/2004 | Laufer et al. | |
| 6,808,491 B2 | 10/2004 | Kortenbach et al. | |
| 6,818,001 B2 | 11/2004 | Wulfman et al. | |
| 6,821,285 B2 | 11/2004 | Laufer et al. | |
| 6,835,200 B2 | 12/2004 | Laufer et al. | |
| 6,908,427 B2 | 6/2005 | Fleener et al. | |
| 6,997,931 B2 | 2/2006 | Sauer et al. | |
| 7,056,284 B2 | 6/2006 | Martone et al. | |
| 7,063,710 B2 | 6/2006 | Takamoto et al. | |
| 7,063,715 B2 | 6/2006 | Onuki et al. | |
| 7,094,246 B2 | 8/2006 | Anderson et al. | |
| 7,144,401 B2 | 12/2006 | Yamamoto et al. | |
| 7,147,646 B2 | 12/2006 | Dana et al. | |
| 7,153,314 B2 | 12/2006 | Laufer et al. | |
| 7,220,266 B2 | 5/2007 | Gambale | |
| 7,232,445 B2 | 6/2007 | Kortenbach et al. | |
| 7,235,086 B2 | 6/2007 | Sauer et al. | |
| 7,285,130 B2 | 10/2007 | Austin | |
| 7,326,221 B2 | 2/2008 | Sakamoto et al. | |
| 7,344,545 B2 | 3/2008 | Takemoto et al. | |
| 7,347,863 B2 | 3/2008 | Rothe et al. | |
| 7,361,180 B2 | 4/2008 | Saadat et al. | |
| 7,530,985 B2 | 5/2009 | Takemoto et al. | |
| 7,601,161 B1 | 10/2009 | Nobles et al. | |
| 7,618,425 B2 | 11/2009 | Yamamoto et al. | |
| 7,713,277 B2 | 5/2010 | Laufer et al. | |
| 7,722,633 B2 | 5/2010 | Laufer et al. | |
| 7,727,246 B2 | 6/2010 | Sixto, Jr. et al. | |
| 7,736,373 B2 | 6/2010 | Laufer et al. | |
| 7,776,057 B2 | 8/2010 | Laufer et al. | |
| 7,776,066 B2 | 8/2010 | Onuki et al. | |
| 7,842,051 B2 | 11/2010 | Dana et al. | |
| 7,846,180 B2 | 12/2010 | Cerier | |
| 7,857,823 B2 | 12/2010 | Laufer et al. | |
| 7,896,893 B2 | 3/2011 | Laufer et al. | |
| 7,918,867 B2 | 4/2011 | Dana et al. | |
| 7,951,157 B2 | 5/2011 | Gambale | |
| 7,992,571 B2 | 8/2011 | Gross et al. | |
| 7,993,368 B2 | 8/2011 | Gambale et al. | |
| 8,016,840 B2 | 9/2011 | Takemoto et al. | |
| 8,021,376 B2 | 9/2011 | Takemoto et al. | |
| 8,057,494 B2 | 11/2011 | Aufer et al. | |
| 8,062,314 B2 | 11/2011 | Sixto, Jr. et al. | |
| 8,066,721 B2 | 11/2011 | Kortenbach et al. | |
| 8,087,856 B2 | 1/2012 | Reed | |
| 8,105,355 B2 | 1/2012 | Page et al. | |
| 8,211,123 B2 | 7/2012 | Gross et al. | |
| 8,216,253 B2 | 7/2012 | Saadat et al. | |
| 8,226,667 B2 | 7/2012 | Viola et al. | |
| 8,277,468 B2 | 10/2012 | Laufer et al. | |
| 8,287,554 B2 | 10/2012 | Cerier et al. | |
| 8,287,556 B2 | 10/2012 | Gilkey et al. | |
| 8,308,765 B2 | 11/2012 | Saadat et al. | |
| 8,313,496 B2 | 11/2012 | Sauer et al. | |
| 8,361,089 B2 | 1/2013 | Chu | |
| 8,388,632 B2 | 3/2013 | Gambale | |
| 8,425,555 B2 | 4/2013 | Page et al. | |
| 8,454,631 B2 | 6/2013 | Viola et al. | |
| 8,480,691 B2 | 7/2013 | Dana et al. | |
| 8,540,735 B2 | 9/2013 | Mitelberg et al. | |
| 8,551,120 B2 | 10/2013 | Gambale | |
| 8,556,914 B2 | 10/2013 | Vrba | |
| 8,585,720 B2 | 11/2013 | Gross et al. | |
| 8,603,123 B2 | 12/2013 | Todd | |
| 8,632,553 B2 | 1/2014 | Sakamoto et al. | |
| 8,679,136 B2 | 3/2014 | Mitelberg | |
| 8,709,022 B2 | 4/2014 | Stone et al. | |
| 8,764,771 B2 | 7/2014 | Chu | |
| 8,882,785 B2 | 11/2014 | Dicesare et al. | |
| 8,926,634 B2 | 1/2015 | Rothe et al. | |
| 8,992,570 B2 | 3/2015 | Gambale et al. | |
| 9,011,466 B2 | 4/2015 | Overes et al. | |
| 9,050,126 B2 | 6/2015 | Rivers et al. | |
| 9,050,127 B2 | 6/2015 | Bonnette et al. | |
| 9,089,325 B2 | 7/2015 | Mitelberg et al. | |
| 9,125,646 B2 | 9/2015 | Woodard, Jr. et al. | |
| 9,198,562 B2 | 12/2015 | Mitelberg et al. | |
| 9,232,957 B2 | 1/2016 | Adams | |
| 9,320,515 B2 | 4/2016 | Dana et al. | |
| 9,474,536 B2 | 10/2016 | Carrison et al. | |
| 9,486,126 B2 | 11/2016 | West et al. | |
| 9,504,465 B2 | 11/2016 | Chu | |
| 9,510,817 B2 | 12/2016 | Saadat et al. | |
| 9,526,519 B2 | 12/2016 | Kessler et al. | |
| 9,549,728 B2 | 1/2017 | Chu | |
| 9,750,494 B2 | 9/2017 | Gross et al. | |
| 9,788,831 B2 | 10/2017 | Mitelberg | |
| 9,844,366 B2 | 12/2017 | Woodard, Jr. et al. | |
| 9,867,610 B2 | 1/2018 | Mitelberg et al. | |
| 9,931,488 B2 | 4/2018 | Bunch et al. | |

(56) References Cited

U.S. PATENT DOCUMENTS

| | | |
|---|---|---|
| 10,045,871 B2 | 8/2018 | Saadat et al. |
| 10,052,122 B2 | 8/2018 | Higgins et al. |
| 10,130,437 B2 | 11/2018 | Lee et al. |
| 10,143,463 B2 | 12/2018 | Dana et al. |
| 10,194,902 B2 | 2/2019 | Nobles et al. |
| 10,285,731 B2 | 5/2019 | Adams et al. |
| 10,335,142 B2 | 7/2019 | Raybin et al. |
| 10,722,250 B2 | 7/2020 | Tasci et al. |
| 10,736,628 B2 | 8/2020 | Yates et al. |
| 2001/0004700 A1 | 6/2001 | Honeycutt et al. |
| 2001/0037121 A1 | 11/2001 | McGuckin, Jr. et al. |
| 2002/0058956 A1 | 5/2002 | Honeycutt et al. |
| 2002/0107530 A1 | 8/2002 | Sauer et al. |
| 2002/0151917 A1 | 10/2002 | Barry |
| 2002/0161384 A1 | 10/2002 | Wulfman et al. |
| 2003/0093103 A1 | 5/2003 | Malackowski et al. |
| 2003/0204205 A1 | 10/2003 | Sauer et al. |
| 2004/0002699 A1 | 1/2004 | Ryan et al. |
| 2004/0068270 A1 | 4/2004 | Alfred, III |
| 2004/0138706 A1 | 7/2004 | Abrams et al. |
| 2004/0186368 A1 | 9/2004 | Ramzipoor et al. |
| 2005/0004579 A1 | 1/2005 | Schneider et al. |
| 2005/0015021 A1 | 1/2005 | Shiber |
| 2005/0033319 A1 | 2/2005 | Gambale et al. |
| 2005/0240146 A1 | 10/2005 | Nash et al. |
| 2005/0250985 A1 | 11/2005 | Saadat et al. |
| 2006/0074405 A1 | 4/2006 | Malackowski et al. |
| 2006/0074442 A1 | 4/2006 | Noriega et al. |
| 2006/0142775 A1 | 6/2006 | Heneberry et al. |
| 2006/0282094 A1 | 12/2006 | Stokes et al. |
| 2007/0093841 A1 | 4/2007 | Hoogland |
| 2007/0239140 A1 | 10/2007 | Chechelski et al. |
| 2007/0270908 A1 | 11/2007 | Stokes et al. |
| 2008/0039823 A1 | 2/2008 | Shimogami et al. |
| 2008/0086148 A1 | 4/2008 | Baker et al. |
| 2008/0097499 A1 | 4/2008 | Nash et al. |
| 2008/0146965 A1 | 6/2008 | Privitera et al. |
| 2009/0024085 A1 | 1/2009 | To et al. |
| 2009/0069829 A1 | 3/2009 | Shturman |
| 2009/0124975 A1 | 5/2009 | Oliver et al. |
| 2009/0177031 A1 | 7/2009 | Surti et al. |
| 2010/0125276 A1 | 5/2010 | Palermo |
| 2010/0137681 A1 | 6/2010 | Ewers et al. |
| 2010/0198006 A1 | 8/2010 | Greenburg et al. |
| 2010/0312263 A1 | 12/2010 | Moberg et al. |
| 2011/0077673 A1 | 3/2011 | Grubac et al. |
| 2011/0213391 A1 | 9/2011 | Rivers et al. |
| 2011/0251554 A1 | 10/2011 | Romoscanu |
| 2011/0306995 A1 | 12/2011 | Moberg |
| 2012/0053606 A1 | 3/2012 | Schmitz et al. |
| 2012/0095461 A1 | 4/2012 | Herscher et al. |
| 2012/0130410 A1 | 5/2012 | Tal et al. |
| 2012/0136348 A1 | 5/2012 | Condie et al. |
| 2012/0158023 A1 | 6/2012 | Mitelberg et al. |
| 2012/0172963 A1 | 7/2012 | Ryan et al. |
| 2012/0179167 A1 | 7/2012 | Wenderow et al. |
| 2012/0185031 A1 | 7/2012 | Ryan et al. |
| 2012/0209176 A1 | 8/2012 | Anderson |
| 2012/0271327 A1 | 10/2012 | West et al. |
| 2013/0006248 A1 | 1/2013 | Ellis |
| 2013/0079763 A1 | 3/2013 | Heckel et al. |
| 2013/0096581 A1 | 4/2013 | Gilkey et al. |
| 2013/0103062 A1 | 4/2013 | To et al. |
| 2013/0253552 A1 | 9/2013 | Schoenle et al. |
| 2013/0274657 A1 | 10/2013 | Zirps et al. |
| 2013/0304093 A1 | 11/2013 | Serina et al. |
| 2014/0100574 A1 | 4/2014 | Bono et al. |
| 2014/0128668 A1 | 5/2014 | Cox et al. |
| 2014/0148835 A1 | 5/2014 | Schmitz et al. |
| 2014/0212457 A1 | 7/2014 | Rifai |
| 2014/0222042 A1 | 8/2014 | Kessler et al. |
| 2014/0249554 A1 | 9/2014 | To et al. |
| 2014/0261453 A1 | 9/2014 | Carlson |
| 2014/0277014 A1 | 9/2014 | Higgins et al. |
| 2014/0316447 A1 | 10/2014 | Ellering et al. |
| 2014/0316448 A1 | 10/2014 | Higgins |
| 2014/0316451 A1 | 10/2014 | Higgins et al. |
| 2014/0324052 A1 | 10/2014 | Carrison et al. |
| 2015/0011834 A1 | 1/2015 | Ayala et al. |
| 2015/0073448 A1 | 3/2015 | Rydberg |
| 2015/0125807 A1 | 5/2015 | Shipley |
| 2015/0126983 A1 | 5/2015 | Alvarado et al. |
| 2015/0164540 A1 | 6/2015 | Higgins et al. |
| 2015/0173776 A1 | 6/2015 | Burke et al. |
| 2015/0173838 A1 | 6/2015 | Murphy et al. |
| 2015/0201956 A1 | 7/2015 | Higgins et al. |
| 2015/0216554 A1 | 8/2015 | Kessler et al. |
| 2015/0327880 A1 | 11/2015 | Wasicek et al. |
| 2015/0335348 A1 | 11/2015 | Cohen et al. |
| 2016/0022307 A1 | 1/2016 | Wasdyke et al. |
| 2016/0045197 A1 | 2/2016 | Mitelberg et al. |
| 2016/0058462 A1* | 3/2016 | Kesten ................... A61B 17/24 |
| | | 606/170 |
| 2016/0157886 A1 | 6/2016 | WasDyke et al. |
| 2016/0235434 A1 | 8/2016 | Smith et al. |
| 2016/0235441 A1 | 8/2016 | Parkin |
| 2016/0287284 A1 | 10/2016 | Smith et al. |
| 2016/0346003 A1* | 12/2016 | Grothe ........... A61B 17/320758 |
| 2016/0354107 A1 | 12/2016 | Nakano et al. |
| 2017/0086817 A1 | 3/2017 | Mitelberg |
| 2017/0086818 A1 | 3/2017 | Mitelberg |
| 2017/0181760 A1 | 6/2017 | Look et al. |
| 2017/0189123 A1 | 7/2017 | Govari et al. |
| 2017/0273698 A1 | 9/2017 | McGuckin, Jr. et al. |
| 2017/0296200 A1 | 10/2017 | Singer et al. |
| 2018/0042602 A1 | 2/2018 | Mitelberg et al. |
| 2018/0042603 A1 | 2/2018 | Mitelberg et al. |
| 2018/0153381 A1 | 6/2018 | Wei et al. |
| 2018/0183179 A1 | 6/2018 | Byrd et al. |
| 2018/0193056 A1 | 7/2018 | Colyer et al. |
| 2018/0235604 A1 | 8/2018 | Comee et al. |
| 2018/0242998 A1 | 8/2018 | Dhandhusaria et al. |
| 2019/0142526 A1 | 5/2019 | Hendrick et al. |
| 2019/0175211 A1 | 6/2019 | Carlson et al. |
| 2019/0262032 A1 | 8/2019 | Carlson et al. |
| 2019/0262034 A1 | 8/2019 | Spangler et al. |
| 2019/0307483 A1* | 10/2019 | Flury ............. A61B 17/320758 |
| 2020/0022764 A1 | 1/2020 | Flexman et al. |
| 2020/0060718 A1 | 2/2020 | Patel et al. |
| 2020/0069324 A1 | 3/2020 | Deepa |
| 2020/0229844 A1 | 7/2020 | Rawson et al. |
| 2020/0315654 A1 | 10/2020 | Patel et al. |
| 2021/0077143 A1 | 3/2021 | Neuharth et al. |
| 2021/0137554 A1 | 5/2021 | Spangler et al. |
| 2021/0172499 A1 | 6/2021 | Nino |
| 2022/0218385 A1 | 7/2022 | Hilse et al. |

FOREIGN PATENT DOCUMENTS

| | | | |
|---|---|---|---|
| EP | 1520509 | A1 | 4/2005 |
| EP | 2011446 | A2 | 7/2009 |
| EP | 2108304 | A2 | 10/2009 |
| EP | 2508141 | A1 | 10/2012 |
| EP | 3053534 | A1 | 8/2016 |
| EP | 3132760 | A1 | 2/2017 |
| EP | 3192461 | A1 | 7/2017 |
| EP | 3222228 | A1 | 9/2017 |
| EP | 3226784 | B1 | 9/2020 |
| IE | 82009529 | A2 | 4/2012 |
| JP | H10174689 | A | 6/1998 |
| JP | 2001509685 | A | 7/2001 |
| WO | 9629014 | A1 | 9/1996 |
| WO | 9814124 | A1 | 4/1998 |
| WO | 0051511 | A1 | 9/2000 |
| WO | 0056230 | A2 | 9/2000 |
| WO | 2001054595 | A1 | 8/2001 |
| WO | 0189393 | A1 | 11/2001 |
| WO | 0249518 | A2 | 6/2002 |
| WO | 2004080507 | A2 | 9/2004 |
| WO | 2008016592 | A2 | 2/2008 |
| WO | 2008045376 | A2 | 4/2008 |
| WO | 2008098124 | A1 | 8/2008 |
| WO | 2010036227 | A1 | 4/2010 |
| WO | 2010056714 | A1 | 5/2010 |

(56)                    References Cited

FOREIGN PATENT DOCUMENTS

| WO | 2010089727 A1 | 8/2010 |
| WO | 2011060192 A1 | 5/2011 |
| WO | 2011106053 A1 | 9/2011 |
| WO | 2013158849 A2 | 10/2013 |
| WO | 2014106847 A1 | 7/2014 |
| WO | 2016001932 A1 | 1/2016 |
| WO | 2016144834 A1 | 9/2016 |
| WO | 2016200811 A1 | 12/2016 |
| WO | 2017087856 A1 | 5/2017 |
| WO | 2018156603 A1 | 8/2018 |
| WO | 2019118522 A1 | 6/2019 |
| WO | 2019168784 A1 | 9/2019 |
| WO | 2020055728 A1 | 3/2020 |
| WO | 2020223433 A1 | 11/2020 |

OTHER PUBLICATIONS

International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
Invitation to Pay Additional Fees dated Nov. 18, 2019 for International Application No. PCT/US2019/049774.
International Search and Written Opinion dated Sep. 20, 2019 for International Application No. PCT/2019/039312.
International Search Report and Written Opinion dated Jun. 4, 2021 for International Application No. PCT/US2021/017939.
International Search Report and Written opinion dated Mar. 28, 2018 for International Application No. PCT/US2018/013587.
International Search Report and Written Opinion dated Apr. 17, 2019 for International Application No. PCT/US2019/018121.

International Search Report and Written Opinion dated Apr. 26, 2019, for International Application No. PCT/US2019/019404.
"What is a PID Controller: Working & Its Applications, 2013, EL-PRO-CUS, URL:https://www.elprocus.com/the-working-of-a-pid-controller/" 17 pages, (Year:2013).
International Search Report and Written Opinion dated Apr. 26, 2019, for International Application No. PCT/US2019/019631.
International Search Report and Written Opinion dated Apr. 26, 2019, for International Application No. PCT/US2019/0198848.
International Search Report and Written Opinion dated Mar. 30, 2020 for International Application No. PCT/US2020/014062.
International Search Report and Written Opinion dated Jun. 25, 2020 for International Application No. PCT/US2020/012767.
International Search Report and Written Opinion dated Apr. 22, 2020 for International Application No. PCT/US2020/013764.
International Search Report and Written Opinion dated Jun. 24, 2020 for International Application No. PCT/US2020/027079.
International Search Report and Written Opinion dated Sep. 4, 2020 for International Application No. PCT/US2020/038132.
International Search Report and Written Opinion dated Sep. 7, 2020 for International Application No. PCT/US2020/038145.
International Search Report and Written Opinion dated Dec. 8, 2020 for International Application No. PCT/US2020/049999.
Invite to Pay Additional Fees dated Feb. 16, 2021 for International Application No. PCT/US2020/061383.
International Search Report and Written Opinion dated Feb. 22, 2022 for International Application No. PCT/US2021/057279.
International Search Report and Written Opinion dated Jan. 26, 2022 for International Application No. PCT/US2021/056616.
International Search Report and Written Opinion for International Application No. PCT/US2022/041260 mailed Oct. 17, 2022, 12 pages.

* cited by examiner

Proximal | Distal

ATHERECTOMY SYSTEM WITH ANTEROGRADE AND RETROGRADE ABLATION

RELATED APPLICATIONS

This application claims the benefit of priority under 35 U.S.C. § 119 of U.S. Provisional Application No. 63/237,679, filed Aug. 27, 2021, the entire disclosure of which is hereby incorporated by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

SUMMARY

This disclosure provides design, material, manufacturing method, and use alternatives for medical devices. As an example, an atherectomy system includes an advancer assembly and a drive assembly that is adapted to translate relative to the advancer assembly. A control knob extends from the drive assembly such that translating the control knob results in the drive assembly translating relative to the advancer assembly. A drive shaft is operably coupled with the drive assembly and translates relative to the advancer assembly as the drive assembly translates relative to the advancer assembly. A feedback modifier is operably coupled between the drive assembly and the advancer assembly and is adapted to provide a user of the atherectomy system with similar feedback via the control knob regardless of whether the user is moving the drive assembly in an anterograde ablation direction or a retrograde ablation direction.

Alternatively or additionally, the drive shaft may include a coil spring having a first set of properties when the coil spring is in compression while ablating in the anterograde ablation direction and a second set of properties when the coil spring is in tension while ablating in the retrograde ablation direction.

Alternatively or additionally, the feedback modifier may be adapted to have little or no impact on the feedback provided to the user when the user moves the drive assembly slowly or with low force.

Alternatively or additionally, the feedback modifier may be adapted to have relatively greater impact on the feedback provided to the user when the user moves the drive assembly more quickly or with high force.

Alternatively or additionally, the feedback modifier may be adapted to have little or no impact on the feedback provided to the user when the user moves the drive assembly in the anterograde ablation direction.

Alternatively or additionally, the feedback modifier may be adapted to have relatively greater impact on the feedback provided to the user when the user moves the drive assembly in the retrograde ablation direction.

Alternatively or additionally, the feedback modifier may include a spring and a dash pot.

Alternatively or additionally, the feedback modifier may include a non-Newtonian damper.

Alternatively or additionally, the feedback modifier may include a first magnet secured relative to the advancer assembly and a second magnet secured relative to the drive assembly such that the first magnet and the second magnet repel each other when the drive assembly is moved in a retrograde ablation direction.

Alternatively or additionally, the first magnet and the second magnet each include a North pole and a South pole and the first magnet and the second magnet are arranged such that either the North pole of the first magnet faces the North pole of the second magnet or the South pole of the first magnet faces the South pole of the second magnet.

Alternatively or additionally, the feedback modifier may include a ferrofluidic coupler having a ferrofluidic fluid that can pass through an orifice within the ferrofluidic coupler, a sensor adapted to provide a condition signal indicative of a current driveshaft condition and a ferrofluidic controller operably coupled with the sensor and the ferrofluidic coupler and adapted to provide an instruction signal to the ferrofluidic coupler, based at least in part upon the condition signal, to modify a force felt by the user.

Alternatively or additionally, the instruction signal may instruct the ferrofluidic coupler to change a viscosity of the ferrofluidic fluid.

Alternatively or additionally, the feedback modifier may include an electro hydraulic coupler having hydraulic fluid that can pass through an orifice having an adjustable diameter, a sensor adapted to provide a condition signal indicative of a current driveshaft condition and an electro hydraulic controller operably coupled with the sensor and the electro hydraulic coupler, the electro hydraulic controller adapted to provide an instruction signal, based at least upon the condition signal, to the electro hydraulic coupler to adjust the diameter of the orifice to modify a force felt by the user.

Alternatively or additionally, the atherectomy system may further include an atherectomy burr adapted for both anterograde ablation and retrograde ablation.

Alternatively or additionally, the atherectomy burr may include a tapered body including a proximal taper and a distal taper, a first ablating surface disposed on the proximal taper for retrograde ablation and a second ablating surface disposed on the distal taper for anterograde ablation.

As another example, an atherectomy system includes an advancer assembly and a drive assembly that is adapted to translate relative to the advancer assembly. A flexible drive shaft is operably coupled with the drive assembly, the flexible drive shaft translating relative to the advancer assembly as the drive assembly translates relative to the advancer assembly. A feedback modifier is operably coupled between the drive assembly and the advancer assembly. The feedback modifier is adapted to provide the user with linear feedback through the drive assembly when the user moves the drive assembly in an anterograde ablation direction and to provide the user with feedback that emulates the linear feedback through the drive assembly when the user moves the drive assembly in a retrograde direction.

Alternatively or additionally, the feedback modifier may be adapted to have little or no impact on the feedback provided to the user when the user moves the drive assembly slowly or with low force and to have relatively greater impact on the feedback provided to the user when the user moves the drive assembly more quickly or with high force.

Alternatively or additionally, the feedback modifier may be adapted to have little or no impact on the feedback provided to the user when the user moves the drive assembly in the anterograde ablation direction and to have relatively greater impact on the feedback provided to the user when the user moves the drive assembly in the retrograde ablation direction.

As another example, an atherectomy system includes an advancer assembly and a drive assembly that is adapted to translate relative to the advancer assembly. A drive shaft is operably coupled with the drive assembly and translates relative to the advancer assembly as the drive assembly translates relative to the advancer assembly. An electromechanical feedback modifier is operably coupled between the drive assembly and the advancer assembly, the electromechanical feedback modifier adapted to provide a user of the atherectomy system with similar feedback via the control knob regardless of whether the user is moving the drive assembly in an anterograde ablation direction or a retrograde ablation direction.

Alternatively or additionally, the drive shaft may include a coil spring having a first set of properties when ablating in the anterograde ablation direction and a second set of properties when ablating in the retrograde ablation direction.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
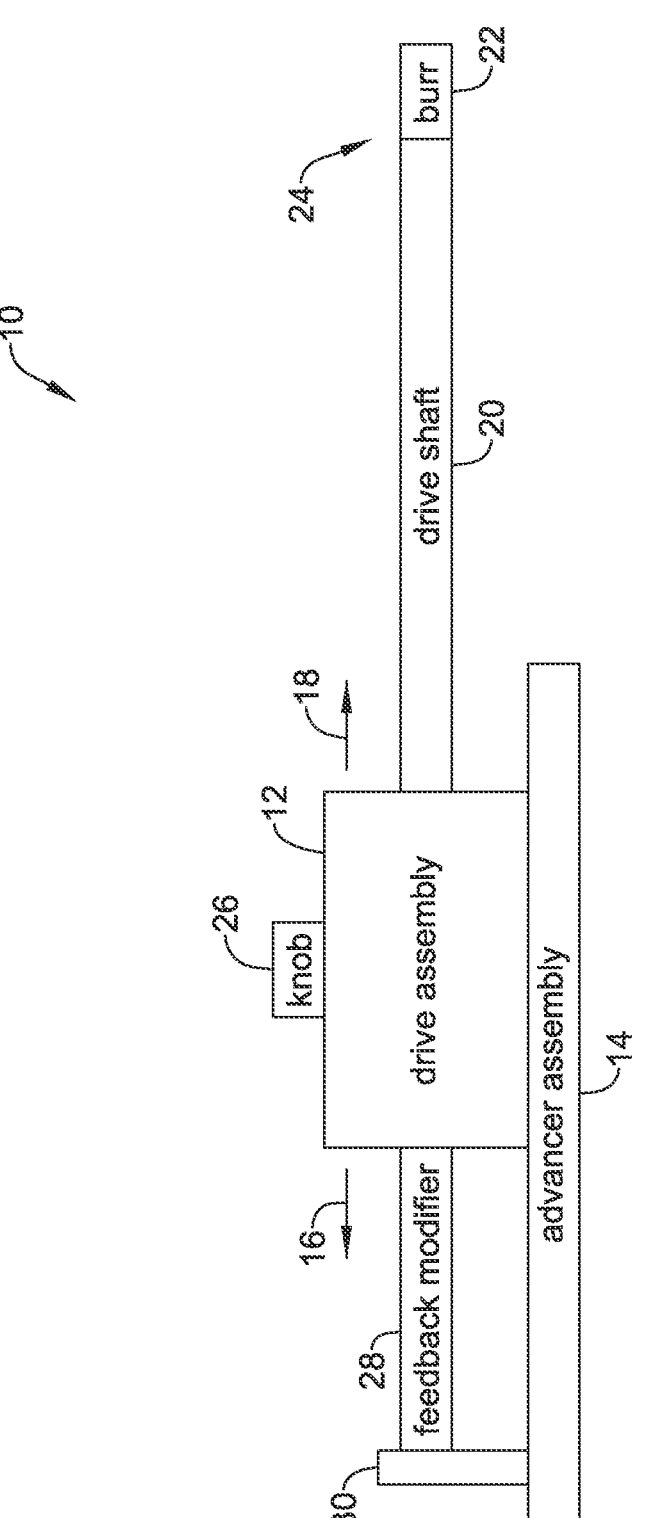
FIG. 1 is a schematic block diagram of an illustrative atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits may restrict blood flow and can cause ischemia in a heart of a patient, vasculature of a patient's legs, a patient's carotid artery, etc. Such ischemia may lead to pain, swelling, wounds that will not heal, amputation, stroke, myocardial infarction, and/or other conditions.

Atheromatous deposits may have widely varying properties, with some deposits being relatively soft and others being fibrous and/or calcified. In the latter case, the deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and/or a variety of catheter-based approaches that may rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material (e.g., blocked by an occlusion). In an atherectomy procedure, a device on an end of a drive shaft that is used to engage and/or remove (e.g., abrade, grind, cut, shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction. In some cases, atherectomy involves using an abrasive atherectomy burr that is rotated at high speeds exceeding 100,000 revolutions per minute (RPM) in order to abrade plaque and other hardened materials from within the patient's vessel. Atherectomy burrs may be rotated at speeds exceeding 140,000 RPM, at speeds exceeding 180,000 RPM and even at speeds as high as 220,000 RPM. Atherectomy may include orbital atherectomy in addition to rotational atherectomy.

FIG. 1 is a schematic block diagram of an illustrative atherectomy system 10. The illustrative atherectomy system 10 includes a drive assembly 12 that is adapted to be translatingly secured relative to an advancer assembly 14. In some cases, the advancer assembly 14 may be adapted to be fixed in space, such as being secured to a table, for example. In some cases, the advancer assembly 14 may be part of an advancer handle. The drive assembly 12 may also be disposed within an advancer handle, for example, but is adapted to translate back and forth (left and right in the illustrated orientation) as indicated by arrows 16 and 18, respectively. A drive shaft 20 extends distally from the drive assembly 12. An atherectomy burr 22 is secured to a distal end 24 of the drive shaft 20. While not illustrated, the drive shaft 20 includes a lumen that allows the drive shaft 20 to be advanced over a guidewire to reach a treatment site as well as to rotate with respect to the guidewire. A knob 26 is secured to the drive assembly 12 such that moving the knob 26 back and forth in the directions indicated by the arrows 16 and 18 causes the drive assembly 12 to move back and forth in the directions indicated by the arrows 16 and 18.

The drive assembly 12 may include a drive motor, such as an electric drive motor, a pneumatic drive motor, a hydraulic drive motor or even a windup drive motor. In some cases, the drive motor may not be disposed within the drive assembly 12, but may instead be remotely located, with a flexible drive cable extending from the drive motor to the drive assembly 12. In some cases, the drive motor and other components, such as but not limited to a controller that is adapted to regulate operation of the drive motor, may be disposed in a reusable assembly that either remains outside of the sterile field during use, or may be bagged or otherwise sealed for use within the sterile field. In some cases, a reusable assembly may be adapted to be sterilized a plurality of times and thus can be used for more than one patient. In some cases, at least some of the drive assembly 12, the advancer assembly 14, the drive shaft 20 and the atherectomy burr 22 may be considered as being part of a single use assembly, that is sterilizable for use with a single patient and then is disposed of. In some cases, the entire atherectomy system 10 may be considered to be adapted for single use. In some cases, the entire atherectomy system 10 may be considered to be adapted for multiple uses.

In some cases, the drive shaft 20 is a coil spring. It will be appreciated that a coil spring may have a first set of properties when under compression, such as when the drive shaft 20 is being advanced distally and the atherectomy burr 22 has reached an obstacle, and may have a second set of properties that are different from the first set of properties when under tension, such as when the drive shaft 20 is being withdrawn proximally and the atherectomy burr 22 has reached an obstacle. In some cases, while the drive shaft 20 is intended to rotate in a particular rotational direction when being used to drive the atherectomy burr 22, instances of excessive torque may cause the atherectomy system 10 to behave differently. For example, the controller regulating operation of the drive assembly 12 may stop the drive shaft 20 and may briefly reverse its rotational direction. It will be appreciated that this may cause the drive shaft 20 to alternate between winding, when driven in its primary direction, and unwinding, when either driven in a rotational direction opposite its primary direction or allowed to unwind on its own. It will be appreciated that the feel of the atherectomy system 10, as manifested in the force the user feels when trying to move the knob 26, may not be consistent depending on what the drive shaft 20 is doing.

In some cases, the atherectomy system 10 may provide a particular feedback to the user when the user is using the atherectomy system 10 to ablate in an anterograde direction, meaning advancing the atherectomy burr 22 in a distal direction into a lesion to be removed or reduced. In some cases, the feedback provided to the user during ablation in an anterograde direction provides predictability, i.e., the user learns to recognize how the feedback the user is receiving via the force the user is applying to the knob 26 translates into what the drive shaft 20 is doing. The user learns that a particular application of force via the knob 26 means that moving the atherectomy burr 22 a particular distance, for example. The feedback when ablating in the anterograde direction may be considered as largely being "linear". However, in some cases there may be a desire to also be able to ablate in a retrograde direction, i.e., while moving the atherectomy burr 22 in a proximal direction. This may come about if the user applies too much force, and the atherectomy burr 22 pops through the lesion and ends up distal of the lesion. This is referred to as "watermelon seeding" the atherectomy burr 22. Alternatively or additionally, once a lesion is removed or reduced while ablating in an anterograde direction, the atherectomy burr 22 may be translated distal to the lesion, such that on translation in the proximal direction, the atherectomy burr 22 is able to ablate in the retrograde direction. This is known as "polishing" the lesion. Ablation in both the anterograde direction and the retrograde direction can be advantageous relative to polishing solely in the anterograde direction.

Ablating in a retrograde direction may provide the user with feedback that is less predictable and less "linear". Accordingly, there is a risk of providing too much force, which can cause potential tissue damage or even cause the atherectomy burr 22 to become stuck and in some instances occlude blood flow. In some cases, the atherectomy system 10 may include a feedback modifier 28, schematically shown as extending between an extension 30 of the advancer assembly 14 and the drive assembly 12. The feedback modifier 28 may take any of a variety of forms, as will be discussed, and may serve to adjust or modify the feedback that the user receives while moving the knob 26, particularly when trying to move the atherectomy burr 22 in a proximal direction. The particular location of the feedback modifier 28, relative to the drive assembly 12 and the advancer assembly 14, is merely schematic, and is not intended to be limiting in any fashion or to imply any particular physical relationship between the components. The feedback modifier 28 may include a single component, or may include multiple components that are disposed at various positions within the atherectomy system 10. The feedback modifier 28 is adapted to emulate the feedback expected during anterograde ablation, even if the user is performing retrograde ablation.

Figure 2:
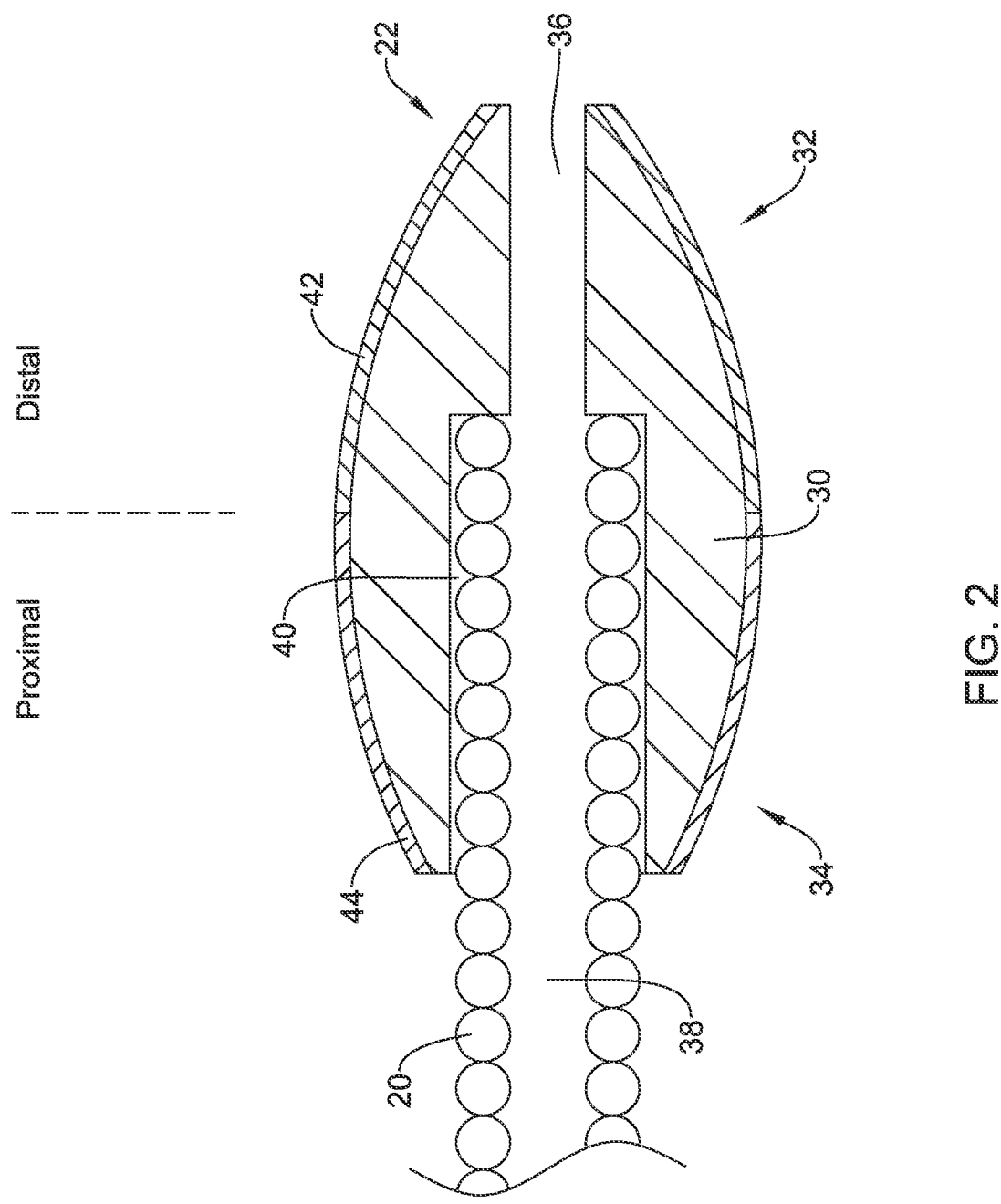
FIG. 2 is a schematic block diagram of an illustrative atherectomy burr.

In order to perform retrograde ablation, and as seen for example in FIG. 2, the atherectomy burr 22 may be adapted for performing both anterograde ablation and retrograde ablation. The atherectomy burr 22 may be seen as having an ovoid body 30 including a distal tapered portion 32 and a proximal tapered portion 34. The atherectomy burr 22 includes a lumen 36 that aligns with a corresponding lumen 38 extending through the drive shaft 20 in order to accommodate a guidewire (not shown). The atherectomy burr 22 includes a void 40 that is adapted to accommodate the drive shaft 20 and to secure the atherectomy burr 22 relative to the drive shaft 20. The atherectomy burr 22 may be adhesively secured, for example, or may be welded or soldered into place. An abrasive material 42, such as but not limited to diamonds, may be disposed over the distal tapered portion 32. An abrasive material 44, such as but not limited to diamonds, may be disposed over the proximal tapered portion 34. Accordingly, the atherectomy burr 22 may be considered as being adapted for both anterograde ablation and retrograde ablation.

Figure 3:
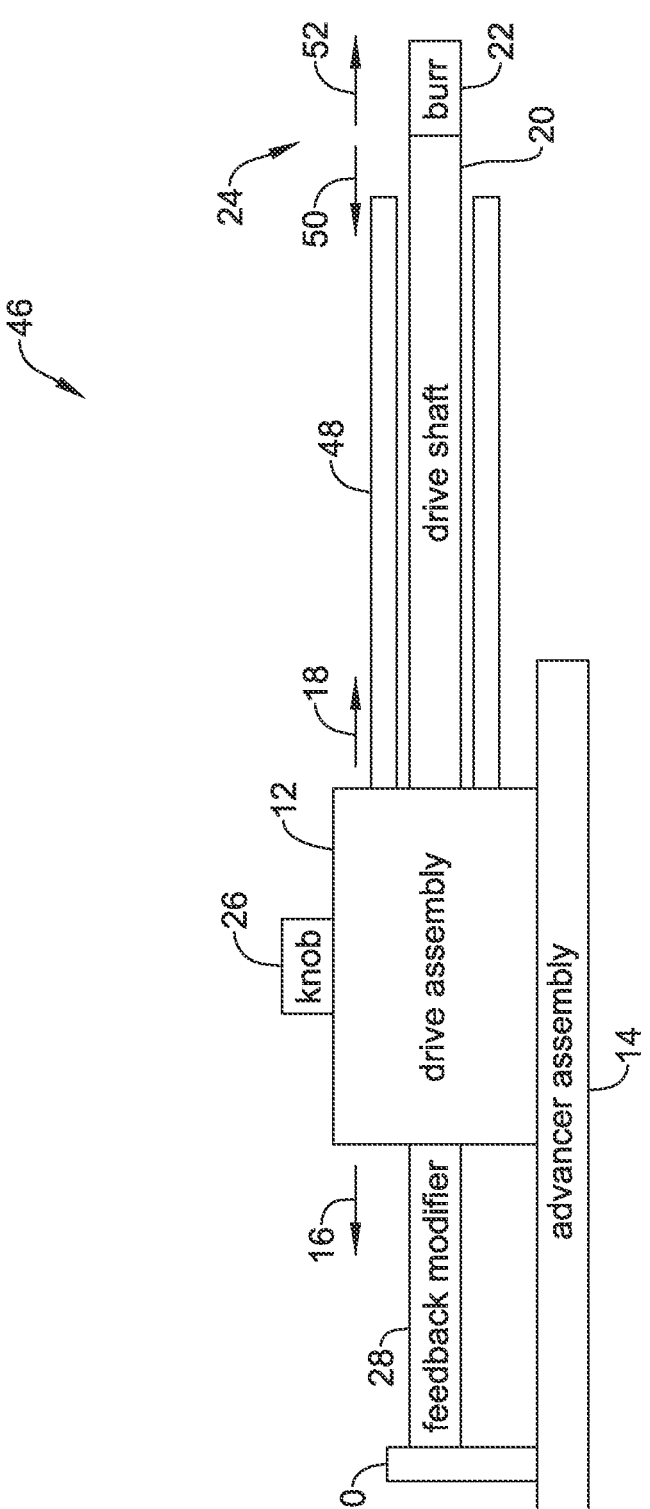
FIG. 3 is a schematic block diagram of an illustrative atherectomy system.

It will be appreciated that the drive shaft 20 may include additional components. FIG. 3 is a schematic block diagram showing an illustrative atherectomy system 46. The illustrative atherectomy system 46 may be considered as being an example of the atherectomy system 10 shown in FIG. 1. As shown in FIG. 3, there is an outer sheath 48 disposed over the drive shaft 20 such that the drive shaft 20 is able to rotate within the outer sheath 48. As shown in FIG. 3, the outer sheath 48 may be considered as being secured relative to the drive assembly 12 such that the outer sheath 48 translates left and right, in directions indicated by arrows 50 and 52, respectively, when the drive assembly 12 translates left and right in the directions indicated by the arrows 16 and 18, respectively. This means that the position of the atherectomy burr 22 relative to the outer sheath 48 does not change.

Figure 4:
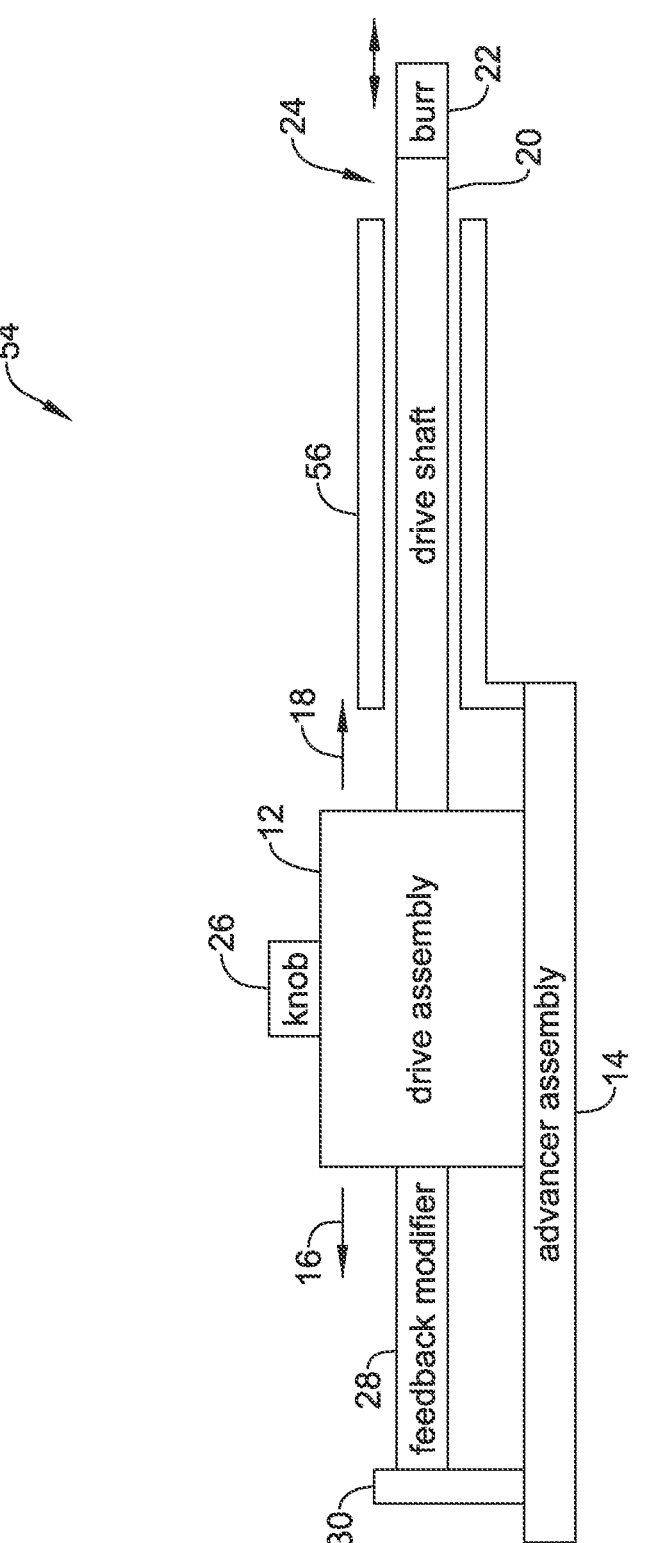
FIG. 4 is a schematic block diagram of an illustrative atherectomy system.

FIG. 4 is a schematic block diagram of an illustrative atherectomy system 54. The atherectomy system 54 may be considered as being an example of the atherectomy system 10 shown in FIG. 1. As shown in FIG. 4, there is an outer sheath 56 disposed over the drive shaft 20 such that the drive shaft 20 is able to rotate within the outer sheath 56. As shown in FIG. 4, the outer sheath 56 may be considered as being secured relative to the advancer assembly 14 such that the outer sheath 56 remains stationary while the drive assembly 12 translates left and right in the directions indicated by the arrows 16 and 18, respectively. This means that the position of the atherectomy burr 22 relative to the outer sheath 56 does change.

Figure 5:
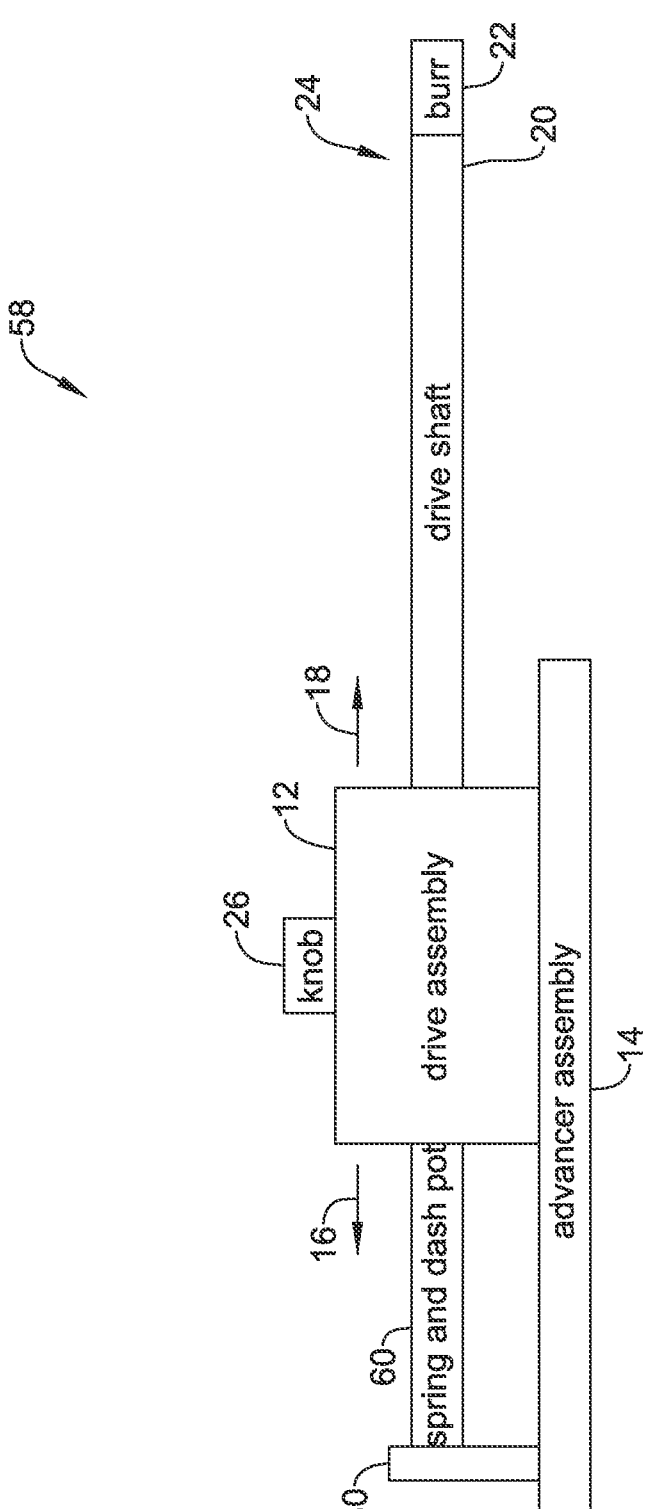
FIG. 5 is a schematic block diagram of an illustrative atherectomy system.

FIG. 5 is a schematic block diagram of an illustrative atherectomy system 58. The atherectomy system 58 may be considered as being an example of the atherectomy system 10 shown in FIG. 1. While not shown, the atherectomy system 58 may include an outer sheath such as the outer sheath 48 (FIG. 3) or the outer sheath 56 (FIG. 4). The atherectomy system 58 includes a spring and dashpot 60 as an example of the feedback modifier 28 shown in FIG. 1. The relative position of the spring and dashpot 60, as shown in FIG. 5, is merely illustrative. The spring and dashpot 60 is adapted to modify the force and tactile feel felt by the user interfacing with the knob 26.

A dashpot is a mechanical device, a damper that resists motion via viscous friction. The resulting force applied by the dashpot may be proportional to velocity, but in the opposite direction. Thus, the dashpot slows the motion. If the knob 26 is moved slowly, the dashpot will have little impact on applied force. However, if the knob 26 is moved more quickly, a greater opposing force may be applied. A spring may be included in order to resist displacement. In some cases, the spring and dashpot 60 may function similarly to how a shock absorber functions on a car or truck, for example. In some cases, it is contemplated that the spring and dashpot 60 may include one or more valves or other mechanisms that may cause damping to be different, depending on the direction of movement. In some cases, possible adjustments may include high and low speed compression rate, rebound rate and preload, for example.

Figure 6:
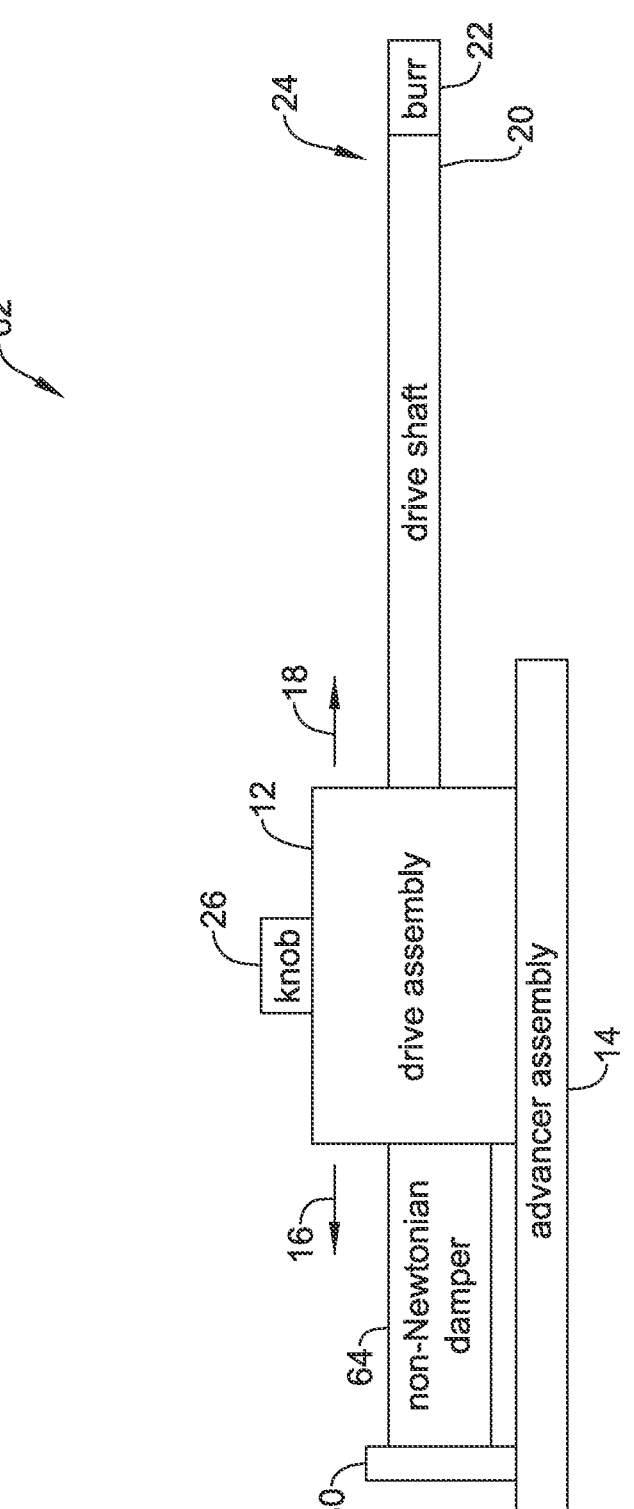
FIG. 6 is a schematic block diagram of an illustrative atherectomy system.

FIG. 6 is a schematic block diagram of an illustrative atherectomy system 62. The atherectomy system 62 may be considered as being an example of the atherectomy system 10 shown in FIG. 1. While not shown, the atherectomy system 62 may include an outer sheath such as the outer sheath 48 (FIG. 3) or the outer sheath 56 (FIG. 4). The atherectomy system 62 includes a non-Newtonian damper 64 as an example of the feedback modifier 28 shown in FIG. 1. In some ways, the non-Newtonian damper 64 functions in a manner similar to that of the spring and dashpot 60 shown in FIG. 5.

The non-Newtonian damper 64 includes a non-Newtonian fluid. A non-Newtonian fluid is a fluid that does not follow Newton's law of viscosity, i.e., constant viscosity independent of stress. In a non-Newtonian fluid, viscosity can change when under force to either be more liquid or more solid. Non-Newtonian fluids may be dilatant, meaning that the viscosity increases when shear is applied (known as shear thickening), or pseudoplastic, in which viscosity decreases with applied shear (known as shear thinning). In some cases, the non-Newtonian damper 64 includes a dilatant fluid.

The non-Newtonian fluid within the non-Newtonian damper 64 allows the user to move the knob 26 in order to engage and disengage the atherectomy burr 22 with atherosclerotic material inside of diseased vessel with little or no additional force when moved slowly. When moved more quickly, however, the non-Newtonian fluid will provide increased force against movement of the knob 26. As a result, the force applied to the atherectomy burr 22 is limited, protecting the patient. The relative position of the non-Newtonian damper 64 is merely illustrative.

Figure 7:
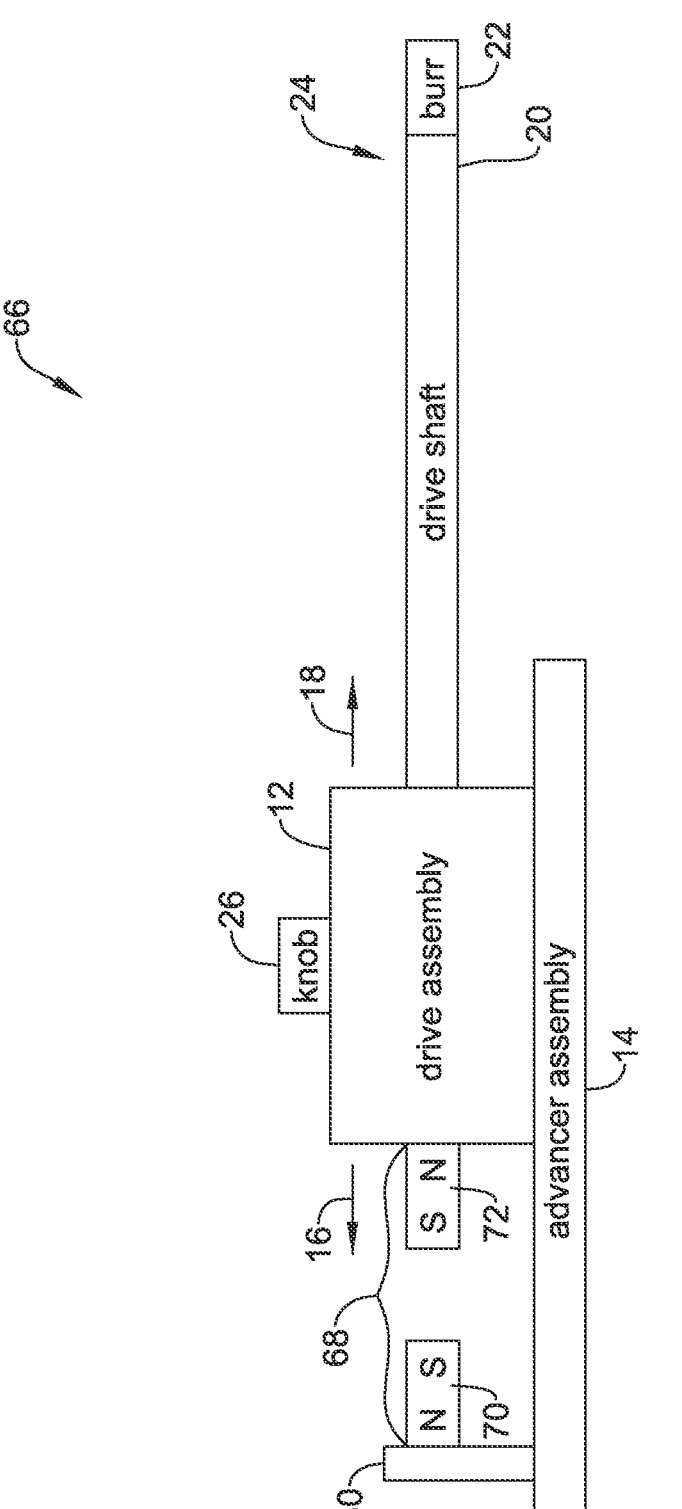
FIG. 7 is a schematic block diagram of an illustrative atherectomy system.

FIG. 7 is a schematic block diagram of an illustrative atherectomy system 66. The atherectomy system 66 may be considered as being an example of the atherectomy system 10 shown in FIG. 1. While not shown, the atherectomy system 66 may include an outer sheath such as the outer sheath 48 (FIG. 3) or the outer sheath 56 (FIG. 4). The atherectomy system 66 includes a magnetic damper 68 as an example of the feedback modifier 28 shown in FIG. 1. The relative position of the magnetic damper 68 is merely illustrative.

In some cases, the magnetic damper 68 includes a first magnet 70 that is secured relative to the extension 30 of the advancer assembly 14 and a second magnet 72 that is secured relative to the drive assembly 12 such that the second magnet 72 moves away from the first magnet 70 when the knob 26 is moved distally, in the direction indicated by the arrow 18, and the second magnet 72 moves towards the first magnet 72 when the knob 26 is moved proximally, in the direction indicated by the arrow 16.

As will be appreciated, each of the first magnet 70 and the second magnet 72 include a North pole and a South pole. As shown, the first magnet 70 and the second magnet 72 are both positioned with their respective South poles closest to each other. As a result, as the drive assembly 12 moves proximally, the second magnet 72 is moved closer to the first magnet 70. As the distance between the first magnet 70 and the second magnet 72 decreases, there will be an increasing repelling force provided by the two South poles moving into proximity with each other. The closer they get, the stronger the force. Thus, as the drive assembly 12 is moved proximally by moving the knob 26, the relative force felt by the user will increase. The increased force helps the user to know they should apply less force to the knob 26 in order to not stall the atherectomy burr 22, which can be deleterious to the patient.

The first magnet 70 and the second magnet 72 may also be positioned with their respective North poles closest to each other, with the same result. As the second magnet 72 moves away from the first magnet 70, such as when the distal assembly 12 moves distally, the impact of the magnetic damper 68 will lessen substantially. The first magnet 70 and the second magnet 72 may each be permanent magnets. In some cases, one or both of the first magnet 70 and the second magnet 72 may be electromagnets that can be selectively turned on or off, if desired. In some cases, the magnetic fields may be fixed or actively controlled in order to achieve desired speed, force and displacement characteristics.

Figure 8:
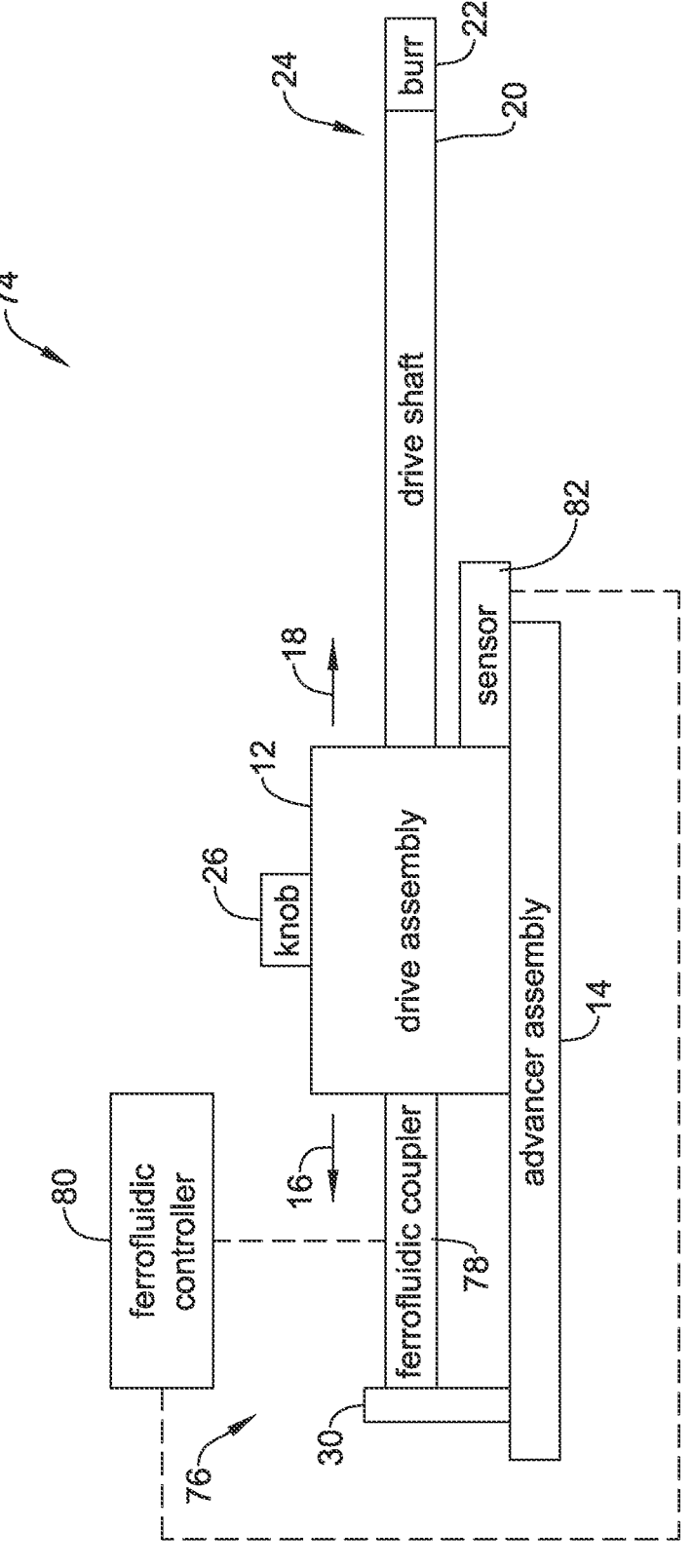
FIG. 8 is a schematic block diagram of an illustrative atherectomy system.

FIG. 8 is a schematic block diagram of an illustrative atherectomy system 74. The atherectomy system 74 may be considered as being an example of the atherectomy system 10 shown in FIG. 1. While not shown, the atherectomy system 74 may include an outer sheath such as the outer sheath 48 (FIG. 3) or the outer sheath 56 (FIG. 4). The atherectomy system 74 includes a ferrofluidic coupler assembly 76 as an example of the feedback modifier 28 shown in FIG. 1. The relative position of the individual components forming the ferrofluidic coupler assembly 76 are merely illustrative.

The ferrofluidic coupler assembly 76 includes a ferrofluidic coupler 78 that can modify the force and tactile feel felt by the user interfacing with the knob 26. The ferrofluidic coupler assembly 76 includes a ferrofluidic controller 80 that may be distinct from any controller that is otherwise regulating operation of the atherectomy system 74. In some cases, the ferrofluidic controller 80 may be part of or otherwise incorporated into any controller that is otherwise regulating operation of the atherectomy system 74. In some cases, the ferrofluidic controller 80 may provide feedback to any controller that is otherwise regulating operation of the atherectomy system 74. Similarly, the controller regulating operation of the atherectomy system 74 may provide feedback to the ferrofluidic controller 80. The ferrofluidic controller 80 is operably coupled with a sensor 82 that is adapted to provide the ferrofluidic controller 80 with a sensor input pertaining to operation of the drive shaft 20. This may include one or more of a current position of the drive shaft 20, a current direction of movement of the drive shaft 20, the force being applied to the drive shaft 20, the force being applied to or by the atherectomy burr 22, and others.

The ferrofluidic controller 80 is also operably coupled with the ferrofluidic coupler 78 such that the ferrofluidic controller 80 can provide an electrical signal to the ferrofluidic coupler 78 in order to modify the force felt by the user via the knob 26. The ferrofluidic controller 80 may instruct the ferrofluidic coupler 78 to provide more or less force, depending on the electrical signal provided by the sensor 82. The ferrofluidic coupler 78 may operate magnetically. The ferrofluidic coupler 78 may change a viscosity of a ferrofluidic fluid passing through an aperture within the ferrofluidic coupler 78. When the viscosity of the fluid increases, a greater resistance to movement of the knob 26 is felt by the user, thereby helping the user to know to apply less force to the knob 26, and thus the lesion, so as to avoid possible situations of the burr sticking or getting stuck. When the viscosity of the fluid decreases, a relatively lesser resistance to knob motion is felt by the user.

Figure 9:
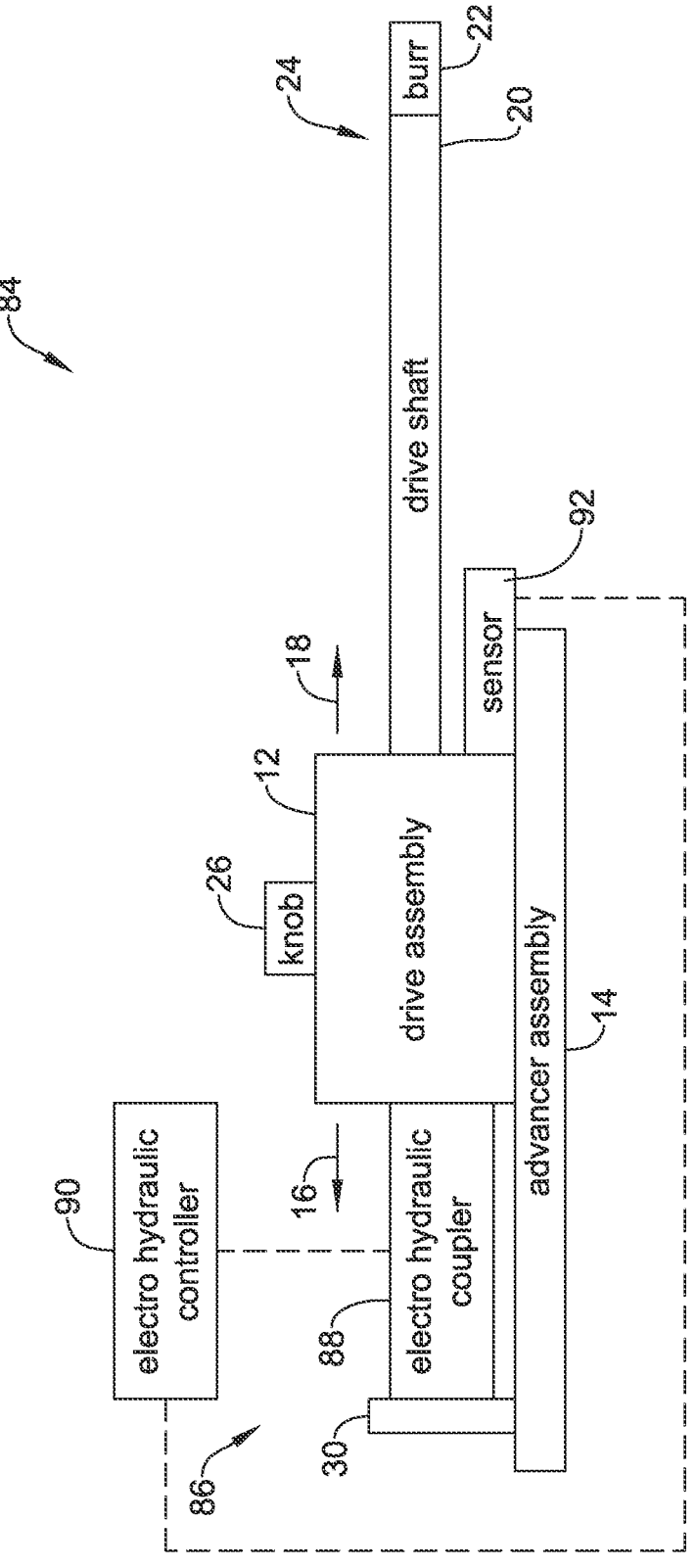
FIG. 9 is a schematic block diagram of an illustrative atherectomy system.

FIG. 9 is a schematic block diagram of an illustrative atherectomy system 84. The atherectomy system 84 may be considered as being an example of the atherectomy system 10 shown in FIG. 1. While not shown, the atherectomy system 84 may include an outer sheath such as the outer sheath 48 (FIG. 3) or the outer sheath 56 (FIG. 4). The atherectomy system 84 includes an electro hydraulic coupler assembly 86 as an example of the feedback modifier 28 shown in FIG. 1. The relative position of the individual components forming the electro hydraulic coupler assembly 86 are merely illustrative.

The electro hydraulic coupler assembly 86 includes an electro hydraulic coupler 88 that can modify the force and tactile feel felt by the user interfacing with the knob 26. The electro hydraulic assembly 86 includes an electro hydraulic controller 90 that may be distinct from any controller that is otherwise regulating operation of the atherectomy system 84. In some cases, the electro hydraulic controller 90 may be part of or otherwise incorporated into any controller that is otherwise regulating operation of the atherectomy system 84. In some cases, the electro hydraulic controller 90 may provide feedback to any controller that is otherwise regulating operation of the atherectomy system 84. Similarly, the controller regulating operation of the atherectomy system 84 may provide feedback to the electro hydraulic controller 90. The electro hydraulic controller 90 is operably coupled with a sensor 92 that is adapted to provide the electro hydraulic controller 90 with a sensor input pertaining to operation of the drive shaft 20. This may include one or more of a current position of the drive shaft 20, a current direction of movement of the drive shaft 20, the force being applied to the drive shaft 20, the force being applied to or by the atherectomy burr 22, and others.

The electro hydraulic controller 90 is also operably coupled with the electro hydraulic coupler 88 such that the electro hydraulic controller 90 can provide an electrical signal to the electro hydraulic coupler 88 in order to modify the force felt by the user via the knob 26. The electro hydraulic controller 90 may instruct the electro hydraulic coupler 88 to provide more or less force, depending on the electrical signal provided by the sensor 92. The electro hydraulic coupler 88 may electrically alter the size of an orifice within the electro hydraulic coupler 88 through which a fluid passes.

In some cases, the electro hydraulic coupler 88 may be considered as being a dynamically controllable spring and dashpot system, similar to that discussed with respect to FIG. 5. Changing the orifice dimensions as a response to sensor input can change the compression and rebound rate of the electro hydraulic coupler 88. As the drive assembly 12 translates to ablate in the anterograde and retrograde directions, the sensor 92 and the electro hydraulic controller 90 can dynamically alter the compression rate and hence the resistance force felt by the user through the knob 26 so that the user may know to apply less force to the knob 26, and hence the lesion, so as to avoid possible situations with burr stall or burr stick. The compression rate may be different in anterograde and retrograde motion direction. As a result, the electro hydraulic coupler 88 can compensate for what might otherwise be a less linear feedback when moving and/or ablating in the retrograde direction, thereby making the feedback feel more linear.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An atherectomy system, comprising:

an advancer assembly;

a drive assembly adapted to translate relative to the advancer assembly;

a control knob extending from the drive assembly such that translating the control knob results in the drive assembly translating relative to the advancer assembly;

a drive shaft operably coupled with the drive assembly, the drive shaft translating relative to the advancer assembly as the drive assembly translates relative to the advancer assembly; and a feedback modifier operably coupled between the drive assembly and the advancer assembly, the feedback modifier adapted to provide a user of the atherectomy system with similar feedback via the control knob regardless of whether the user is moving the drive assembly in an anterograde ablation direction or a retrograde ablation direction;

wherein the feedback modifier comprises:

a ferrofluidic coupler having a ferrofluidic fluid that can pass through an orifice within the ferrofluidic coupler;

a sensor adapted to provide a condition signal indicative of a current driveshaft condition;

and a ferrofluidic controller operably coupled with the sensor and the ferrofluidic coupler, the ferrofluidic controller adapted to provide an instruction signal to the ferrofluidic coupler, based at least in part upon the condition signal, to modify a force felt by the user.

2. The atherectomy system of claim 1, wherein the drive shaft comprises a coil spring having a first set of properties when the coil spring is in compression while ablating in the anterograde ablation direction and a second set of properties when the coil spring is in tension while ablating in the retrograde ablation direction.

3. The atherectomy system of claim 1, wherein the feedback modifier is adapted to have little or no impact on the feedback provided to the user when the user moves the drive assembly slowly or with low force.

4. The atherectomy system of claim 3, wherein the feedback modifier is adapted to have relatively greater impact on the feedback provided to the user when the user moves the drive assembly more quickly or with high force.

5. The atherectomy system of claim 1, wherein the feedback modifier is adapted to have little or no impact on the feedback provided to the user when the user moves the drive assembly in the anterograde ablation direction.

6. The atherectomy system of claim 5, wherein the feedback modifier is adapted to have relatively greater impact on the feedback provided to the user when the user moves the drive assembly in the retrograde ablation direction.

7. The atherectomy system of claim 1, wherein the instruction signal instructs the ferrofluidic coupler to change a viscosity of the ferrofluidic fluid.

8. The atherectomy system of claim 1, further comprising an atherectomy burr adapted for both anterograde ablation and retrograde ablation.

9. The atherectomy system of claim 8, wherein the atherectomy burr comprises:

a tapered body including a proximal taper and a distal taper;

a first ablating surface disposed on the proximal taper for retrograde ablation; and a second ablating surface disposed on the distal taper for anterograde ablation.

10. An atherectomy system, comprising:

an advancer assembly;

a drive assembly adapted to translate relative to the advancer assembly;

a control knob extending from the drive assembly such that translating the control knob results in the drive assembly translating relative to the advancer assembly;

a drive shaft operably coupled with the drive assembly, the drive shaft translating relative to the advancer assembly as the drive assembly translates relative to the advancer assembly; and a feedback modifier operably coupled between the drive assembly and the advancer assembly, the feedback modifier adapted to provide a user of the atherectomy system with similar feedback via the control knob regardless of whether the user is moving the drive assembly in an anterograde ablation direction or a retrograde ablation direction;

wherein the feedback modifier comprises:

an electro hydraulic coupler having hydraulic fluid that can pass through an orifice having an adjustable diameter;

a sensor adapted to provide a condition signal indicative of a current driveshaft condition;

and an electro hydraulic controller operably coupled with the sensor and the electro hydraulic coupler, the electro hydraulic controller adapted to provide an instruction signal, based at least upon the condition signal, to the electro hydraulic coupler to adjust the diameter of the orifice to modify a force felt by the user.

11. The atherectomy system of claim 10, wherein the drive shaft comprises a coil spring having a first set of properties when the coil spring is in compression while ablating in the anterograde ablation direction and a second set of properties when the coil spring is in tension while ablating in the retrograde ablation direction.

12. The atherectomy system of claim 10, wherein the feedback modifier is adapted to have little or no impact on the feedback provided to the user when the user moves the drive assembly slowly or with low force.

13. The atherectomy system of claim 12, wherein the feedback modifier is adapted to have relatively greater impact on the feedback provided to the user when the user moves the drive assembly more quickly or with high force.

14. The atherectomy system of claim 10, wherein the feedback modifier is adapted to have little or no impact on the feedback provided to the user when the user moves the drive assembly in the anterograde ablation direction.

15. The atherectomy system of claim 14, wherein the feedback modifier is adapted to have relatively greater impact on the feedback provided to the user when the user moves the drive assembly in the retrograde ablation direction.

16. The atherectomy system of claim 10, further comprising an atherectomy burr adapted for both anterograde ablation and retrograde ablation.

17. The atherectomy system of claim 16, wherein the atherectomy burr comprises:

a tapered body including a proximal taper and a distal taper;

a first ablating surface disposed on the proximal taper for retrograde ablation; and a second ablating surface disposed on the distal taper for anterograde ablation.

* * * * *